United States Patent
Vilsmeier et al.

(10) Patent No.: US 7,561,733 B2
(45) Date of Patent: Jul. 14, 2009

(54) PATIENT REGISTRATION WITH VIDEO IMAGE ASSISTANCE

(75) Inventors: Stefan Vilsmeier, Munich (DE); Johannes Manus, München (DE)

(73) Assignee: BrainLAG AG, Feldkirchen (DE)

( * ) Notice: Subject to any disclaimer, the term of this patent is extended or adjusted under 35 U.S.C. 154(b) by 693 days.

(21) Appl. No.: 11/274,944

(22) Filed: Nov. 15, 2005

(65) Prior Publication Data

US 2006/0173357 A1 Aug. 3, 2006

Related U.S. Application Data

(60) Provisional application No. 60/645,400, filed on Jan. 19, 2005.

(30) Foreign Application Priority Data

Nov. 15, 2004 (EP) .................................. 04027075

(51) Int. Cl.
*G06K 9/00* (2006.01)
*G06K 9/32* (2006.01)
*A61B 6/00* (2006.01)
*G06K 9/36* (2006.01)

(52) U.S. Cl. ........................ 382/154; 382/294; 382/128; 600/476

(58) Field of Classification Search ................. 382/154, 382/128, 131, 100, 285, 294, 276; 348/42, 348/47, 48; 378/98, 98.2, 98.5, 98.12, 195, 378/198, 206, 208, 205; 600/411, 414, 425, 600/426, 427, 424, 476
See application file for complete search history.

(56) References Cited

U.S. PATENT DOCUMENTS 6,006,126 A * 12/1999 Cosman ...................... 600/426

(Continued)

FOREIGN PATENT DOCUMENTS

WO 01/59708 A1 8/2001

OTHER PUBLICATIONS

Cohlchester, A.C.F. et al.; "Development and preliminary evalutation of VISLAN, a surgical planning and guidance system using intraoperative video image", Medical Image Analysis, Bd. 1, Nr. 1, 1996, pp. 73-90, XP002322964.

(Continued)

*Primary Examiner*—Yon Couso
(74) *Attorney, Agent, or Firm*—Renner, Otto, Boisselle & Sklar, LLP

(57) ABSTRACT

A method and device for reciprocally assigning a spatial position of a patient and/or a part of a patient's body and an acquired, stored patient data set includes producing at least two video image recordings of the patient and/or part of the body from different recording positions via at least one video image source, wherein a three-dimensional position and/or orientation of the video image source relative to a reference coordinate system is known or can be determined. Corresponding tuples of points are identified in the video image recordings, and three-dimensional spatial positions are ascertained and stored from the identified tuples of points. The stored patient data set are matched to a point set of the assigned spatial positions, and a reciprocal assignment or registration of the spatial position of the patient and/or part of the body and the patient data set is determined when the greatest or best match has been achieved.

28 Claims, 4 Drawing Sheets

U.S. PATENT DOCUMENTS

| | | |
|---|---|---|
| 6,744,914 B1 * | 6/2004 | Rubbert et al. .............. 382/154 |
| 7,155,316 B2 * | 12/2006 | Sutherland et al. .......... 700/248 |
| 7,167,738 B2 * | 1/2007 | Schweikard et al. ........ 600/407 |
| 7,203,277 B2 * | 4/2007 | Birkenbach et al. ........ 378/98.5 |
| 2002/0188194 A1 | 12/2002 | Cosman |

OTHER PUBLICATIONS

Bankman, I.N.; "Handbook of Medical Imaging—Processing and Analysis", 2000, Academic Press, San Diego, pp. 623-633, XP002322965.

* cited by examiner

PATENT REGISTRATION WITH VIDEO IMAGE ASSISTANCE

RELATED APPLICATION DATA

This application claims priority of U.S. Provisional Application No. 60/645,400 filed on Jan. 19, 2005, which is incorporated herein by reference in its entirety.

FIELD OF THE INVENTION

The present invention relates to image guided surgery and, more particularly, to a method and device for patient registration with video image assistance, wherein a spatial position of a patient and a stored patient data set are reciprocally assigned.

BACKGROUND OF THE INVENTION

Imprecise registration equipment such as pointers, which often demand a high degree of computation and/or special equipment, are often replaced by video image sources such as cameras, in order to register a patient and/or a part of a patient's body.

WO 01/59708 A1 discloses a method for the direct registration of two or more two-dimensional optical images to a three-dimensional (3D) image or computer model without prior segmentation of images, including acquiring a plurality of optical images of the object and acquiring three dimensional surface model made up of points on a surface of the object, choosing an initial set of parameters which define the registration between the three dimensional model coordinate system and the optical image coordinate system, measuring the quality of registration using a similarity measure and repeating until a maximum of the similarity measure is found.

SUMMARY OF THE INVENTION

A method and device is provided for reciprocally assigning a spatial position of a patient and/or a part of a patient's body and an acquired, stored patient data set. At least one video image source (e.g., a camera or the like), which can include a tracking reference (e.g., markers or a reference star coupled to the video image source), can be moved within a detection range of a tracking system, wherein the tracking system can detect or otherwise determine a three-dimensional spatial position and/or orientation of the video image source via the tracking reference. More specifically, the tracking system can ascertain the three-dimensional spatial position of the video image source while the video image source obtains a recording. Using the video image source, at least two video image recordings or images of the patient and/or the part of a patient's body can be produced from different recording positions. Preferably, the recordings or images are produced while the video image source is located within the detection range of the tracking system, such that the tracking system knows or can ascertain the location or spatial position of the video image source while the recordings were obtained.

The position of the patient and/or part of the patient's body can be known with respect to a reference coordinate system and/or can be invariable or otherwise fixed with respect to the tracking system. Further, a relative movement of the patient or body part can be ascertained and/or tracked by means of a tracking reference that can be fixed to the patient and/or part of the patient's body. Additionally, the position of the patient and/or part of the patient's body can be ascertained relative to the video image source. If, for example, a tracking reference (e.g., markers or a reference star) is arranged on the patient and/or part of the patient's body, then the tracking system can ascertain the spatial position and/or change in position of the patient and/or part of the patient's body. The spatial position and/or change in position can be ascertained with respect to a reference coordinate system, such that movements and shifts by the patient and/or part of the patient's body can be recognized by the tracking system, and the new position of the patient and/or part of the patient's body then can be determined.

By taking into account the three-dimensional spatial position of the body and/or part of the body and the three-dimensional spatial position of the video image source during the recording process, it is possible to determine the position of the at least one video image source relative to the patient and/or part of the patient's body during the recording process. Thus, the position of the patient and/or part of the patient's body and/or the position of the video image source can be known, or the absolute spatial position of the body and/or part of the patient's body and the absolute spatial position of the video image source and the position of the at least one video image source relative to the body and/or part of the patient's body can be ascertained by means of the tracking system.

Corresponding points or tuples of points and/or characteristic points, such as landmark points, can be identified in the video image recordings or obtained images. Since the spatial position of the recorded body and/or part of the body can be known or ascertained by the tracking system, and/or the spatial position of the video image source during the recording process can be known or ascertained by the tracking system, three-dimensional spatial positions, which can be output and/or stored, may be assigned to the points or landmark points. If, for example, corresponding tuples of points or a number of corresponding points are assigned to three-dimensional spatial positions, then a scatter plot or point set of spatial positions can be created. The acquired, stored patient data set, via computer assistance, then can be matched to the point set of the assigned spatial positions.

For example, the stored data set can be matched to the point set by placing the points of the scatter plot or point set of assigned spatial positions over the corresponding points in the patient data set, such that they virtually lie at least approximately at the same location or at least approximately over each other. The distances between each point from the point set and the corresponding points of the patient data set can be ascertained and virtually compared. Alternatively, the distances between each point and the corresponding points of the patient data set can be ascertained until the distance between the points from the point set and corresponding points in the patient data set has reached a minimum value or has been minimized by means of metrics. If points in the patient data set do not directly correspond to points in the point set (e.g., due to the three-dimensional points being arbitrarily scattered), then a virtual surface also can be ascertained, calculated or generated from the acquired, stored patient data set, wherein the distance or distance value between the points of the point set of the assigned spatial positions and the virtual surface of the patient and/or part of the patient's body can be minimized by means of metrics. For example, the distances between each point from the point set and the virtual surface, such as corresponding positions on the virtual surface, can be ascertained and the distances or distance values can be determined until a high match probability between the points of the point set and the virtual surface has been achieved. Alternatively, the distances or distance values can be determined until the distance or distance values between the points of the point set and the virtual surface have reached a minimum value.

The minimum value of the distances between the points of the point set and the corresponding points in the patient data set or the virtual surface generated from the points in the patient data set can be ascertained in a variety of ways. For example, the minimum distance value between the two point sets or between the point set and the virtual surface can be ascertained by comparing or matching the point set of the assigned spatial positions to the corresponding points of the stored patient data set or to the virtual surface until the root of the sum of all the distance squares between the corresponding points or the points of the point set and the corresponding points or locations on the virtual surface have been minimized. In other words, the minimum distance mean value or mean value of the distances between the corresponding points of the point set of the assigned spatial positions and the points of the patient data set or the minimum distance mean value between the points of the point set and the respectively corresponding points on the virtual surface can be ascertained as a distance minimum value. A type of median value also can be used as the distance minimum value, such that the minimum distance value may be determined as the value at which at least approximately 50% of all the distances or distance values of the points corresponding to each other are larger and smaller than the minimum distance value.

Irrespective of which definition of the minimum value is used, when the greatest possible match between the point set of the assigned spatial positions and the corresponding points of the patient data set or the corresponding locations on the virtual surface has been achieved or the distance minimum value has been achieved, the reciprocal assignment or registration of the spatial position of the patient and/or part of the body and the patient data set can be determined, such that the recorded patient and/or part of the patient's body can be registered with respect to the acquired, stored patient data set.

In order to perform the registration, a type of point matching can be used to achieve a best possible match. The method disclosed in WO 01/59708 A1, by contrast, uses a comparison between intensity information of different recorded images and intensity information of a three-dimensional object or its illumination model to achieve the best possible match.

The patient data set can be ascertained using an imaging method such as, for example, a computer tomography method, a nuclear spin tomography method, an ultrasound tomography method, a position emission tomography method or a single photon emission computed tomography (SPECT) method, and the point set of the assigned spatial positions can be stored with computer assistance, e.g. by means of a medical navigation system. The match between the patient data set and the point set also can be established by means of a medical navigation system to which the tracking system is assigned.

In particular, two or more video image sources can be used to record the patient or part of the patient's body and, for example, all of the video image sources can be positioned within the detection range of the tracking system during the recording process. The recordings can be taken simultaneously from different positions or angles of view onto the patient or part of the body. Each of the two or more video image sources can be fixed or immovable and/or resting or movable. The position of the two or more video image sources with respect to each other also can be known, such that at least one, two or all of the video image sources can be located within the detection range of the tracking system, thereby enabling the spatial position of the two or more video image sources and their position during the recording process to be determined.

The two or more video image sources can be located at different spatial positions, for example, to enable the patient and/or part of the patient's body to be simultaneously recorded as video images from different directions or recording positions. The video image source or video image sources can be moved robotically (e.g., by means of one or more robots), for example, such that two or more recordings can be automatically or non-automatically acquired while one or more of the video image sources are not within the detection range of the tracking system during each recording. To this end, the video image sources can be a microscope or endoscope with robotic functions. By attaching the video image source to a mechanical positioning system such as a robot, the position of the at least one video image source can be ascertained, preferably with respect to the reference coordinate system (e.g., by the positioning system independently ascertaining the position or changes in the position of the video image source).

Image feature points and/or landmark points also can be used to assist in identifying the corresponding points or tuples of points, wherein image points of characteristic image features that can enable a corresponding point to be easily located in a subsequent recording can be used as image feature points. Artificial landmark points also can be projected onto, plotted on or attached to the patient and/or part of the patient's body to be recorded, to identify corresponding points or tuples of points, such as landmark points.

Computer-assisted morphing or warping methods also can be used to assist in identifying the corresponding points and/or pairs of points or the landmark points. By morphing or warping one of the video images (e.g., a source image) onto another video image (e.g., a target image) preferably recorded from a different position, corresponding pairs of points or corresponding landmark points in the video images can be automatically detected. Corresponding points can be deduced from the deformation of the source image created during or after the morphing and/or warping process, for example, by finding or identifying as corresponding points or landmark points those points at which no deformation, a low deformation, or the lowest deformation is detected or can be determined. The exactness, smoothness and/or degree of deformation can be described by parameters and, for example, a minimum degree of deformation at a point or pair of points can indicate that there is a corresponding pair of points at the point or pair of points having a minimum degree of deformation.

The point set of the assigned spatial positions also can be assigned to the stored patient data set by a computer-assisted matching method. Using the method, the point set can be substantially matched or matched as far as possible to the patient data set by means of transformations, for example.

Preferably, at least one video camera, which can be registered, navigated and/or tracked by at least two tracking cameras of the tracking system, can be used as the at least one video image source. The method and device, however, are not restricted to optical tracking systems. The video image source can be tracked using any tracking system, such as, for example, a magnetic tracking system. The video image source can be attached to or contained in an existing instrument used in surgery, such as, for example, a surgical microscope or an endoscope.

If, for example, the patient or part of the patient's body is shifted or its shape is changed, as for example in the case of a brain shift, then a re-assignment and/or re-registration can be performed at least in sections by repeating or re-performing the described steps or the described method or parts of the method.

By means of the patient and/or body part registration determined by this method, the position of surgical instruments, their spatial position, their orientation and/or their shape also can be ascertained using the tracking system, and the surgical instrument data can be superimposed onto the patient data and provided graphically via a display, for example.

The method and, in particular, the video image source used in the method, can be operated in various wavelength ranges. The at least one video image source preferably operates in the non-visible wavelength range of light, such as in the infrared range.

The invention further provides a computer program which, when it is loaded onto a computer or is running on a computer, performs a method such as described above. The invention further provides a program storage medium or a computer program product comprising such a program.

A device for patient registration with video image assistance includes at least one video image source, such as a video camera, for producing at least two video image recordings or images of a patient and/or a part of a patient's body from different recording positions. The at least one video image source can be fixed and/or immovable or, alternatively, can be movable. A tracking reference, such as markers or a reference star, can be arranged on (e.g., on top of the video image source) or otherwise coupled to the video image source, such that the three-dimensional spatial position of the video image source can be detected by a tracking system, in particular where the at least one video image source is located during the recording process. Further, the tracking system can detect the spatial position of the body and/or part of the patient's body via a tracking reference, such as markers or a reference star attached to the body.

The device also can include a computational unit, such as a navigation system and/or a computer. The navigation system and/or computer can assign the points or landmark points of the recordings taken by the at least one video image source to three-dimensional spatial positions, and can match a stored patient data set (produced and stored using an imaging method, for example) to the point set of the assigned spatial positions. For example, the stored patient data set can be matched to the point set by calculating and/or comparing the distance between the points from the point set and corresponding points in the patient data set, and comparing the points until a minimum value or a minimum distance value is achieved. The computational unit can include a wireless or wired communications link to the tracking system and/or the at least one video image source, such that the at least one video image source and/or tracking system can transfer data to/from the computational unit. The computational unit also can perform a simulation, for example, wherein the point set or scatter plot of the assigned spatial positions can be placed over the patient data set or the points of the patient data set, such that the distance between the points of the point set of the assigned spatial positions and of the patient data set which correspond to each other is minimized or such that a mean distance value of the points corresponding to each other is minimized.

The device for patient registration with video image assistance can include a data output device that can be connected to the computational unit and can display (e.g., numerically or graphically via a monitor) the patient data set, the point set of the assigned spatial positions and/or the matched data of the point set of the assigned spatial positions and of the patient data set.

The patient data set can be captured by a data input device that can be an imaging device, such as a computer tomograph, a nuclear spin tomograph, an ultrasound tomograph, a position emission tomograph and/or a SPECT tomograph. The data input device can record the patient and/or part of the patient's body and store the recorded data in bulk memory, for example, or in optical memory (e.g, CD or DVD), such that the device can easily read and use the data.

The at least one video image source can be formed to be movable such that its position relative to the patient and the tracking system can be altered. When it is formed to be movable, the at least one video image source can record the body and/or part of the patient's body from different positions, wherein the images recorded from the different positions can be defined or registered with respect to a common coordinate system by taking into account the position of the video image source during the recording process, as detected by the tracking system. The landmark points of the patient and/or part of the patient's body can be detected from different positions using the video image source and registered with respect to a common coordinate system, wherein the tracked video image source can be positioned such that it is detected by the tracking system during the recording process. In particular, the at least one video image source can be positioned such that it can both detect or record the patient and/or part of the patient's body and be detected or tracked itself by the tracking system.

The at least one video image source can be contained in an instrument that can be used in an operation (e.g., a surgical microscope or an endoscope) such that said instrument only need be registered once to enable detection of the patient and/or part of the patient's body and to enable use of the instrument during surgery or during the operation. It is thus not necessary to re-register the instrument.

The device for patient registration with video image assistance also can include two video image sources calibrated with respect to each other. The two video image sources can be configured to be fixed and/or immovable and can be positioned at different spatial locations or positions, such that the angles of view or the recording position of the video image sources differ from each other but are constant or invariable. The two video image sources also can be movable, such that the two video image sources can be freely moved spatially and can be detected by the tracking system, wherein the position of the two video image sources with respect to each other (which due to calibration is known) can be invariable (e.g., due to a link between the video image sources) or can be variable.

The forgoing and other embodiments of the invention are hereinafter discussed with reference to the drawings.

DETAILED DESCRIPTION

Figure 1:
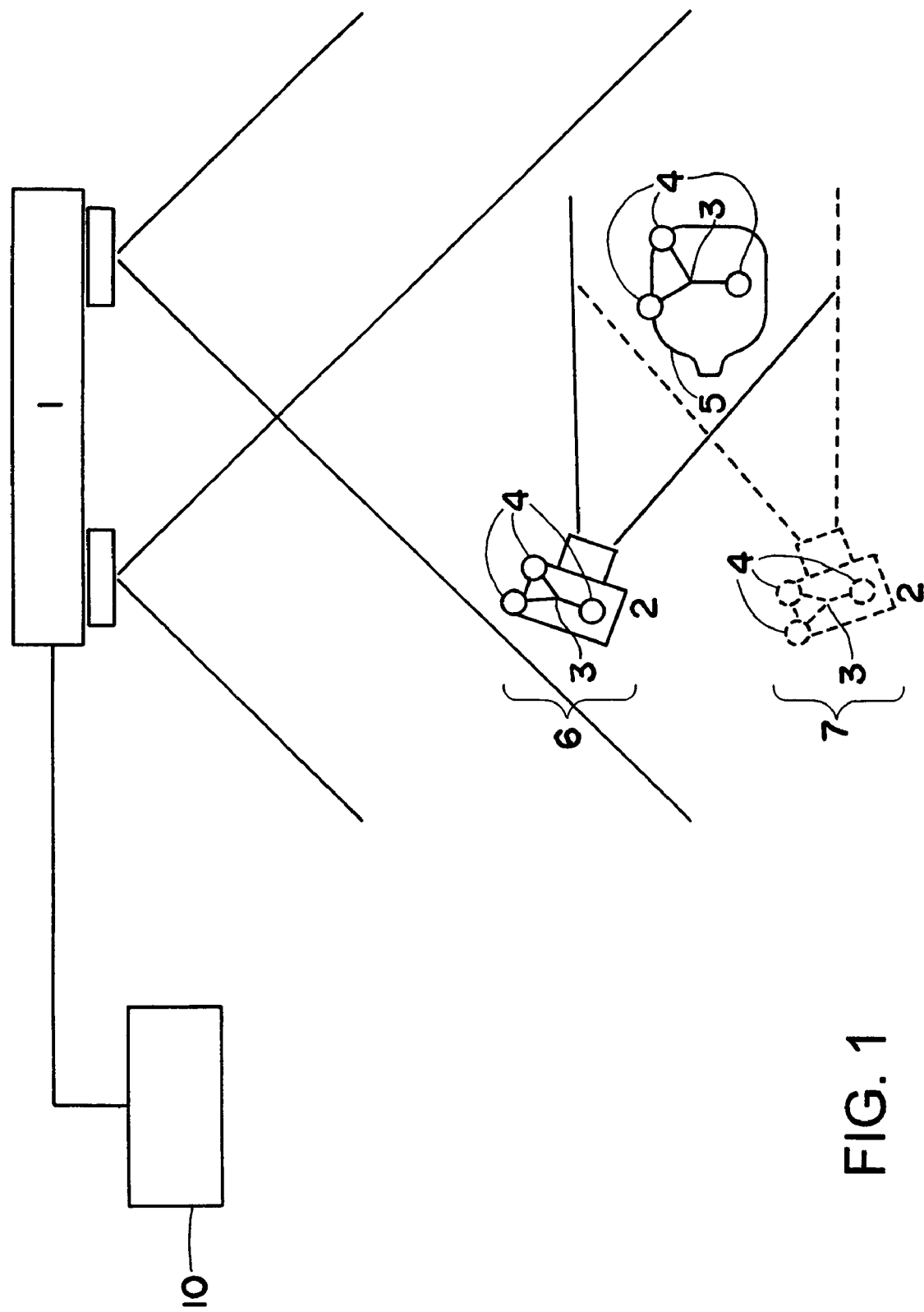
FIG. 1 illustrates an exemplary device in accordance with the present invention.

FIG. 1 shows an exemplary device that includes a tracking system 1, such as a stereoscopic infrared tracking system, a video image source 2, such as a video camera, and an object 5 to be registered, such as a patient's head or body part, for example. A tracking reference 3, for example a reference star having passive reflective markers 4, is attached to the video image source 2 and to the object 5 to be registered. In a first recording position 6, the trackable video image source 2 records the object 5 from one direction or angle of view while the image source 2 is within the detection range of the tracking system 1 (e.g., the image source 2 is within the detection range of both infrared cameras of the tracking system 1), such that the spatial position or recording position 6 of the video image source 2 can be detected by the tracking system 1. In a second recording position 7, the video image source 2 records the object 5 from a different angle of view or from a different position, wherein the video image source 2 is within the detection range of the tracking system 1. Thus, both recording positions 6 and 7 are known to the tracking system 1 and both recordings can be registered, for example, with respect to a common coordinate system by taking into account the respective recording positions 6 and 7. A computer system 10 is communicatively coupled to the tracking system 1 via a wired or wireless link, for example. The computer system 10 may be a stand alone system or may be part of a medical navigation system or the like.

Figure 2:
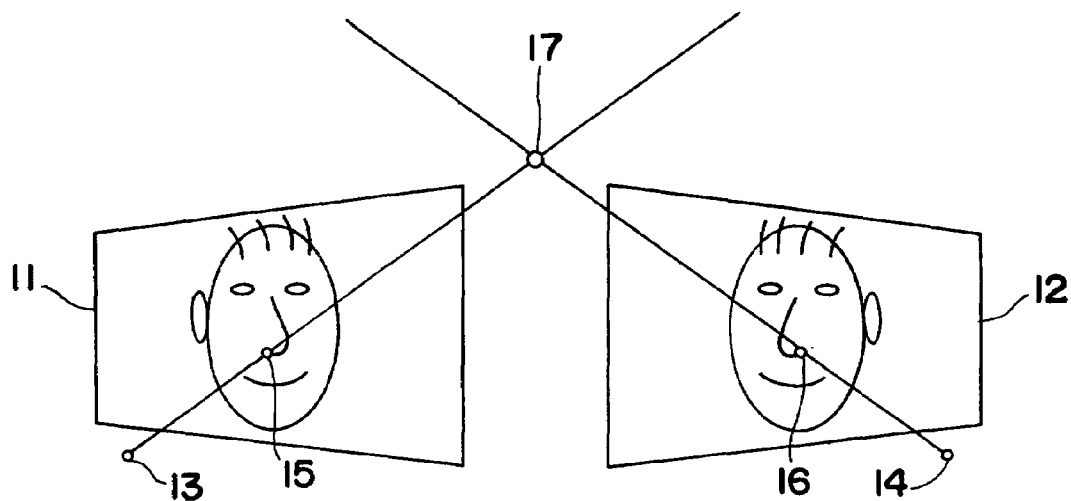
FIG. 2 illustrates two video image recordings from two different recording positions.

FIG. 2 shows the assignment of image points of two different recordings from the two different recordings positions 6 and 7, wherein the assignment can be based on a characteristic landmark point or corresponding tuple of points 15 and 16 in the first and second recording, for example. Since the recording positions 6 and 7 of the video image source 2 during both recordings can be detected by the tracking system 1 and are thus known in a coordinate system, such as a global coordinate system, for example, the landmark point or first point 15 from the first image plane 11, recorded at the first recording position 6 of the video image source 2, and the landmark point or second point 16 of the second image plane 12, recorded at the second recording position 7 of the video image source 2, can be transformed into a common coordinate system, such as the global coordinate system. The transformation can be performed such that the landmark points or corresponding tuple of points 15 and 16 of the two recordings lead to a common reconstructed three-dimensional antecedent point 17 or landmark point in the antecedent or global coordinate system. Each of the corresponding points of the image planes 11 and 12 can be transformed into a common coordinate system or into a common three-dimensional surface point. The three-dimensional surface point 17 generated from the landmark point or corresponding tuple of points 15 and 16 of the two recordings is the intersection point between a first transformation line through the landmark point 15 and the focus point 13 of the first image plane 11 and a second transformation line through the landmark point 16 of the corresponding tuple of points 15 and 16 and the focus point 14 of the second image plane 12. All the landmark points or image points of the recordings of the first image plane 11 and the second image plane 12 thus can be assigned to a three-dimensional spatial position or to an antecedent coordinate system and, therefore, registered as a three-dimensional spatial position with respect to the antecedent or global coordinate system.

Figures 3A, 3B:
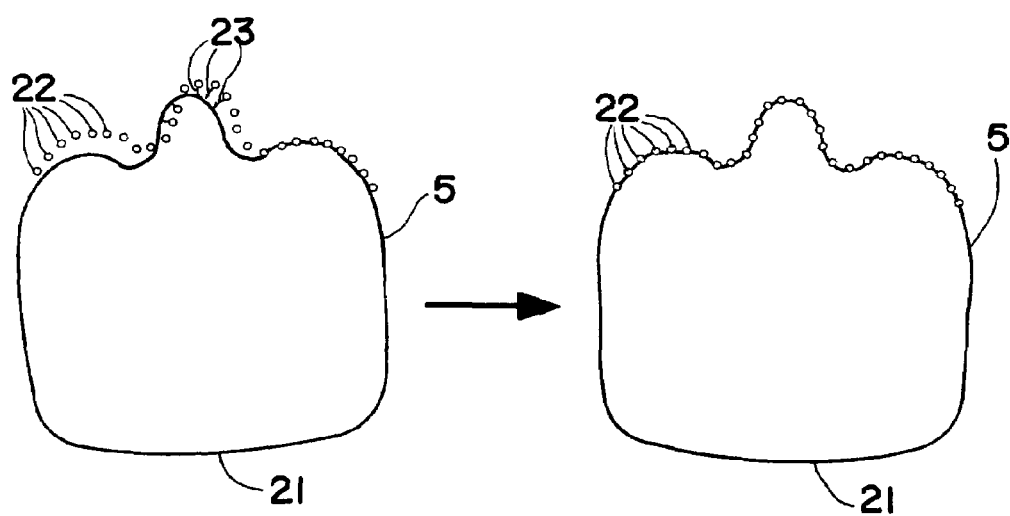
FIGS. 3A and 3B illustrate matching between the patient data set and the point set of the assigned spatial positions.

FIG. 3a shows the surface of an object 5, such as the skin or contour of a patient, for example, which has been obtained by means of an imaging method such as a computer tomography method. The object 5 and/or data corresponding to the object can be secured or stored, for example, in a bulk memory and/or in optical memory. This image data set of the patient or of a part of the patient's body is then matched to the point set of the assigned spatial positions or points 22, such as landmark points, registered with respect to the global coordinate system, wherein there is a distance 23 between the image points 22 and the surface 21 of the object, as can be seen in FIG. 3a. Further, and as also can be seen in FIG. 3b, the reciprocal assignment or registration of the spatial position of the patient and/or part of the body and the patient data set is determined when the greatest match or distance minimum value has been reached, in particular when there is substantially no distance 23 between the points 22 and the surface of the object.

Figure 4:
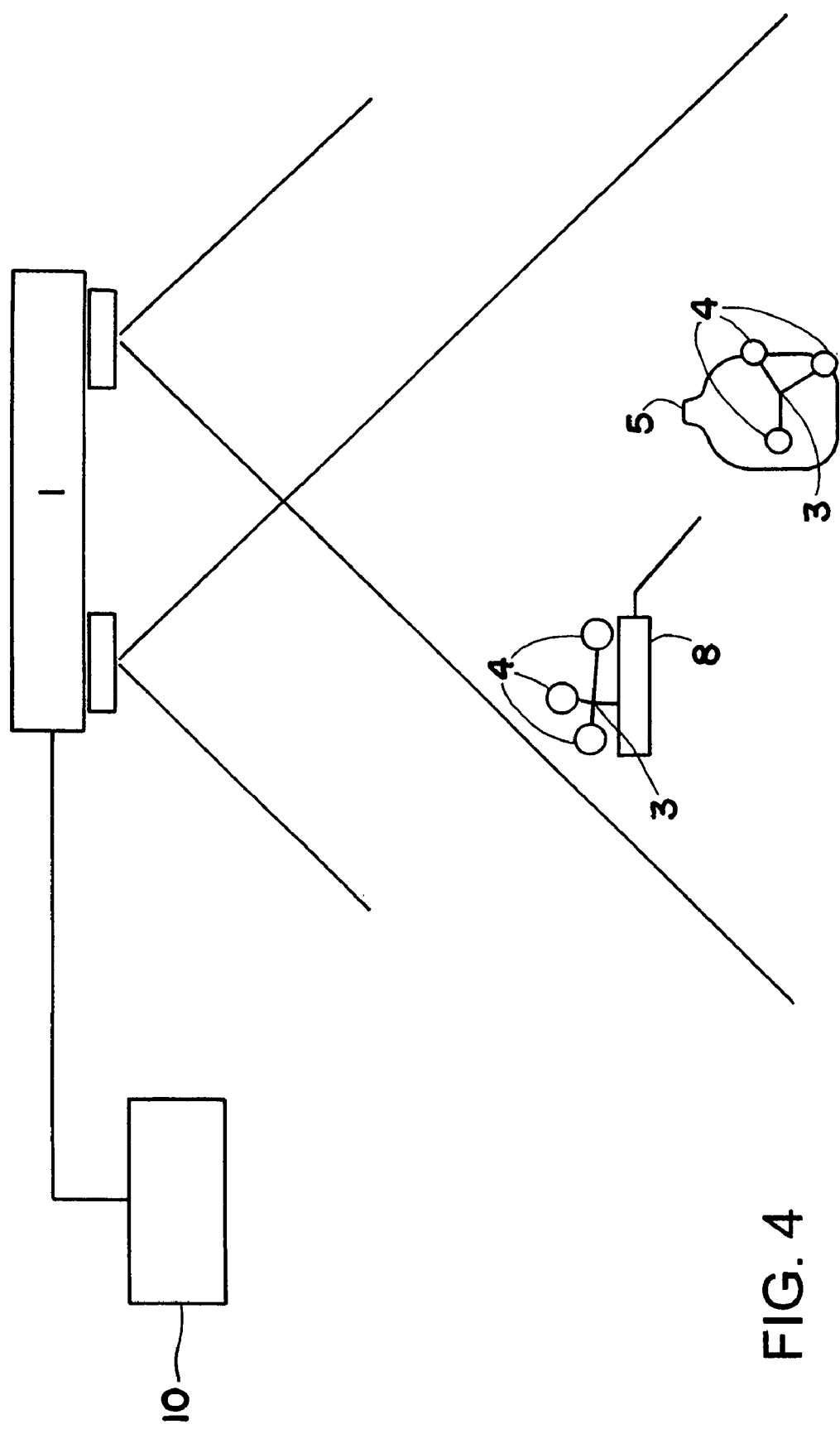
FIG. 4 illustrates another exemplary device in accordance with the present invention.
Figure 5:
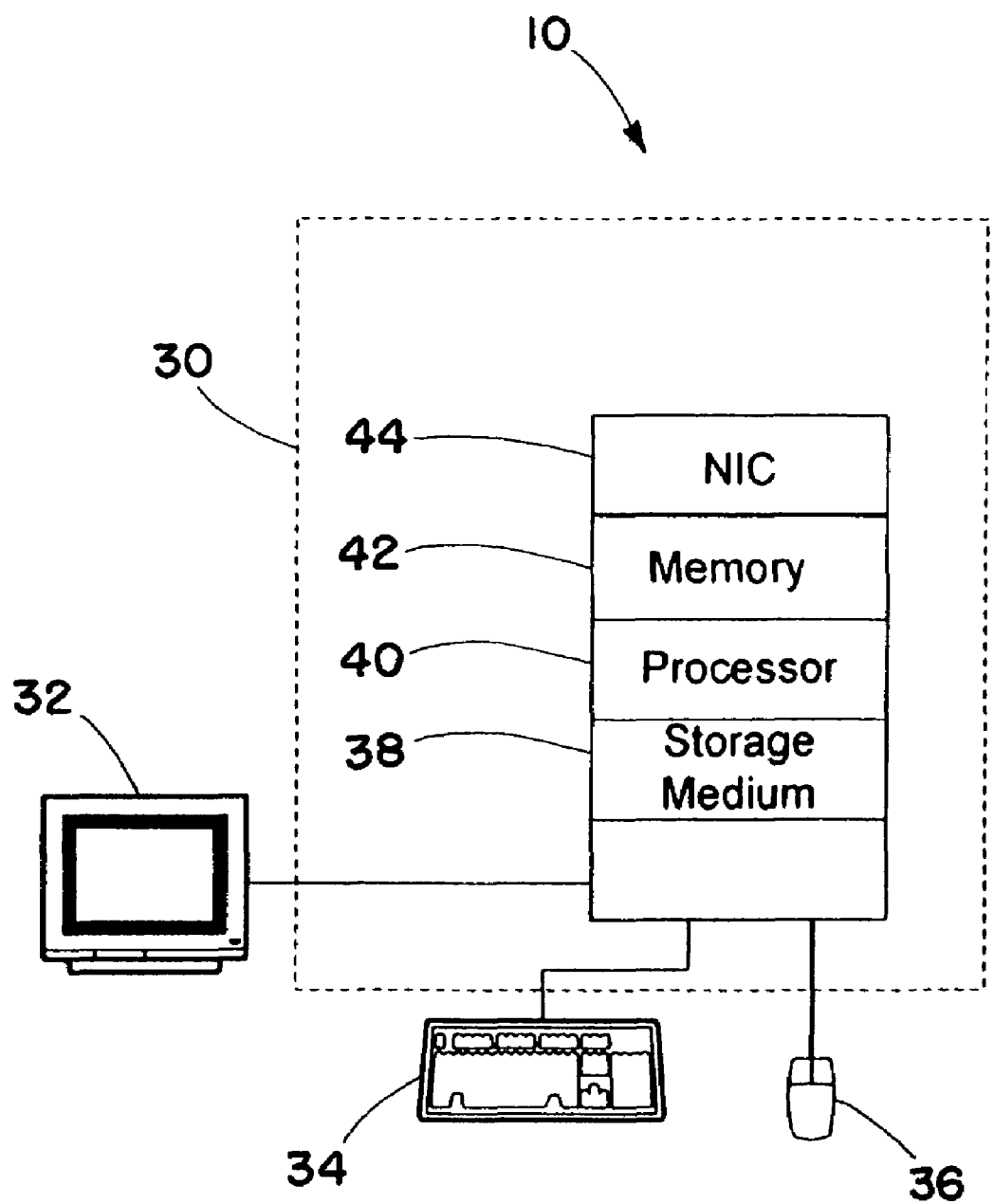
FIG. 5 is a block diagram of a computer system that can be used to implement the method of the present invention.

FIG. 4 shows another embodiment that includes an optical tracking system 1, which can be based on visible light, and a surgical instrument 8, such as, for example, a surgical microscope or an endoscope, which can be used in surgery and preferably includes a video image source such as a camera (not shown). Using the camera, an object 5, such as a patient's head or body part, for example, can be recorded, wherein a tracking reference 3 including markers 4 is arranged on the surgical instrument 8 and on the object 5. The spatial position of the surgical instrument 8 and of the object 5 can be detected by the tracking system 1 via the tracking reference 3 and markers 4. The video image source of the surgical instrument 8 can record at least two video image recordings from different spatial positions. A point set of three-dimensional spatial positions can be ascertained from the video image recordings, and can be registered with respect to the stored data of the object 5, for example, by taking into account the three-dimensional spatial positions of the object 5 and of the surgical instrument 8 or video image source, which can be detected by the tracking system 1.

Moving to FIG. 3, a computer system 10 for executing a computer program in accordance with the present invention is illustrated. The computer system 10 can be communicatively coupled to the tracking system 1 to receive positional data therefrom, and to display three-dimensional positional data. The computer system 10 includes a computer 30 for processing data, and a display 32, such as a CRT, LCD, or the like, for viewing system information. A keyboard 34 and pointing device 36 may be used for data entry, data display, screen navigation, etc. The keyboard 34 and pointing device 36 may be separate from the computer 30 or they may be integral to it. A computer mouse or other device that points to or otherwise identifies a location, action, etc., e.g., by a point and click method or some other method, are examples of a pointing device. Alternatively, a touch screen (not shown) may be used in place of the keyboard 34 and pointing device 36. A touch screen is well known by those skilled in the art and will not be described in detail herein. Briefly, a touch screen implements a thin transparent membrane over the viewing area of the display 32. Touching the viewing area sends a signal to the computer 30 indicative of the location touched on the screen. The computer 30 may equate the signal in a manner equivalent to a pointing device and act accordingly. For example, an object on the display 32 may be designated in software as having a particular function (e.g., view a different screen). Touching the object may have the same effect as directing the pointing device 36 over the object and selecting the object with the pointing device, e.g., by clicking a mouse. Touch screens may be beneficial when the available space for a keyboard 34 and/or a pointing device 36 is limited.

Included in the computer 30 is a storage medium 38 for storing information, such as application data, screen information, programs, etc. The storage medium 38 may be a hard drive, for example. A processor 40, such as an AMD Athlon 64™ processor or an Intel Pentium IV® processor, combined with a memory 42 and the storage medium 38 execute programs to perform various functions, such as data entry, numerical calculations, screen display, system setup, etc. A network interface card (NIC) 44 allows the computer 30 to communicate with devices external to the computer system 10.

The actual code for performing the functions described herein can be readily programmed by a person having ordinary skill in the art of computer programming in any of a number of conventional programming languages based on the disclosure herein. Consequently, further detail as to the particular code itself has been omitted for sake of brevity.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for reciprocally assigning a spatial position of a patient and/or a part of a patient's body and an acquired, stored patient data set, comprising the steps of:
    producing at least two video image recordings of the patient and/or part of the body from different recording positions via at least one video image source, wherein a three-dimensional position and/or orientation of the video image source relative to a reference coordinate system is known or can be determined;
    identifying corresponding tuples of points in the video image recordings;
    ascertaining and storing three-dimensional spatial positions from the identified tuples of points;
    matching the stored patient data set to a point set of the assigned spatial positions;
    determining a reciprocal assignment or registration of the spatial position of the patient and/or part of the body and the patient data set when the greatest or best match has been achieved.

2. The method as set forth in claim 1, wherein matching between the point set and the patient data set is found by minimizing a distance between the points from the point set and corresponding points in the patient data set using metrics.

3. The method as set forth in claim 1, wherein matching between the point set and the patient data set is found by minimizing a distance between the points from the point set and the virtual surface of the patient generated from the patient data set using metrics.

4. The method as set forth in claim 1, wherein the position of the video image source relative to the reference coordinate system is ascertained by attaching a tracking reference to the at least one video image source, the tracking reference located within a detection range of a tracking system.

5. The method as set forth in claim 1, wherein the position of the video image source relative to the reference coordinate system is ascertained by a calibration process.

6. The method as set forth in claim 1, further comprising attaching the video image source to a mechanical positioning system to ascertain the position of the video image source relative to the reference coordinate system.

7. The method as set forth in claim 1, further comprising using a medical navigation system to match and store the patient data set and the point set, wherein a tracking system is assigned to the navigation system.

8. The method as set forth in claim 1, further comprising using two or more video image sources.

9. The method as set forth in claim 1, further comprising using image feature points to assist in identifying the corresponding tuples of points.

10. The method as set forth in claim 1, further comprising projecting on to, plotting on, or attaching to the patient and/or part of the body artificial landmark points to assist in identifying the corresponding tuples of points.

11. The method as set forth in claim 1, further comprising using natural, identifiable landmarks of the patient and/or part of the body as tuples of points.

12. The method as set forth in claim 1, further comprising using a computer-assisted morphing method of the video images to assist in identifying the corresponding tuples of points.

13. The method as set forth in claim 1, wherein matching the stored patient data set to the point set of the assigned spatial positions includes using a computer-assisted matching method.

14. The method as set forth in claim 1, further comprising using at least one video camera as the video image source, wherein the at least one video camera is tracked by at least two tracking cameras of a tracking system.

15. The method as set forth in claim 1, further comprising using at least one video camera as the video image source, wherein the at least one video camera is tracked by a magnetic tracking system.

16. The method as set forth in claim 1, further comprising using a surgical microscope as the video image source.

17. The method as set forth in claim 1, further comprising using an endoscope as the video image source.

18. The method as set forth in claim 1, further comprising performing a re-assignment and/or re-registration at least in sections after the patient or part of the patient's body has been shifted or its shape changed.

19. The method as set forth in claim 1, wherein the at least one video image source is coupled to a medical instrument.

20. The method as set forth in claim 19, wherein the at least one video image source is within the medical instrument.

21. The method as set forth in claim 1, wherein video image source operates in the non-visible range of light.

22. A computer readable medium comprising computer executable instructions adapted to perform the method in accordance with claim 1.

23. A device for patient registration with video image assistance, comprising:
    at least one video image source for recording at least two video images of a patient and/or a part of a patient's body from different recording positions;
    a tracking reference coupled to the video image source; and
    a computational unit that assigns corresponding tuples of points from the at least two recorded video images to three-dimensional spatial positions and substantially matches a stored patient data set to the point set of the assigned spatial positions, wherein said computation unit is connectable to the at least one video image source.

24. The device for patient registration with video image assistance as set forth in claim 23, further comprising:

a tracking system for detecting the three-dimensional spatial position of the video image source, wherein the computational unit substantially matches the stored patient data set to the point set of the assigned spatial positions until a distance between the points from the point set and corresponding points in the patient data set and/or a virtual surface generated from the patient data set reaches a minimum value, wherein said computational unit is connectable to the tracking system and/or the at least one video image source.

25. A computer-readable medium embodied with a computer program for reciprocally assigning a spatial position of a patient and/or a part of a patient's body and an acquired, stored patient data set, comprising code that directs the production of at least two video image recordings of the patient and/or part of the body from different recording positions via at least one video image source, wherein a three-dimensional position and/or orientation of the video image source relative to a reference coordinate system is known or can be determined;

code that identifies corresponding tuples of points in the video image recordings;

code that ascertains and stores three-dimensional spatial positions from the identified tuples of points;

code that matches the stored patient data set to a point set of the assigned spatial positions;

code that determines a reciprocal assignment or registration of the spatial position of the patient and/or part of the body and the patient data set when the greatest or best match has been achieved.

26. The method according to claim 1, further comprising using a tracking system to determine the three-dimensional position of the at least one video image source.

27. The method according to claim 1, further comprising transforming a corresponding tupple of points from the at least two video image recordings into a common coordinate system so as generate a common three-dimensional antecedent point.

28. The method according to claim 1, further comprising transforming a landmark point from the at least two video image recordings into a common coordinate system so as generate a landmark point in the common coordinate system.

* * * * *